(12) United States Patent
Bloom

(10) Patent No.: US 8,263,736 B2
(45) Date of Patent: Sep. 11, 2012

(54) COMPOUNDS AND THEIR EFFECTS ON FEEDING BEHAVIOUR

(75) Inventor: Stephen Robert Bloom, London (GB)

(73) Assignee: Imperial Innovations Limited, London (GB)

( * ) Notice: Subject to any disclaimer, the term of this patent is extended or adjusted under 35 U.S.C. 154(b) by 687 days.

(21) Appl. No.: 12/307,157

(22) PCT Filed: Jul. 3, 2007

(86) PCT No.: PCT/GB2007/002473
§ 371 (c)(1),
(2), (4) Date: Dec. 31, 2008

(87) PCT Pub. No.: WO2008/003947
PCT Pub. Date: Jan. 10, 2008

(65) Prior Publication Data
US 2009/0318347 A1    Dec. 24, 2009

(30) Foreign Application Priority Data

Jul. 3, 2006 (GB) .................................. 0613196.5

(51) Int. Cl.
*C07K 14/00* (2006.01)
(52) U.S. Cl. ......................................... 530/324; 514/5.2
(58) Field of Classification Search .................. 530/324; 514/5.2
See application file for complete search history.

(56) References Cited

U.S. PATENT DOCUMENTS

| | | |
|---|---|---|
| 5,512,549 A | 4/1996 | Chen et al. |
| 6,268,343 B1 * | 7/2001 | Knudsen et al. ............... 514/4.8 |
| 7,459,432 B2 * | 12/2008 | Cowley et al. ................. 514/1.1 |
| 2005/0176643 A1 | 8/2005 | Bridon et al. |
| 2006/0135747 A1 * | 6/2006 | Levy et al. ..................... 530/324 |

FOREIGN PATENT DOCUMENTS

| | | |
|---|---|---|
| EP | 0 708 179 | 4/1996 |
| WO | 03/026591 | 4/2003 |
| WO | 2006/095166 | 9/2006 |

OTHER PUBLICATIONS

International Search Report for PCT/GB2007/002473 mailed Oct. 19, 2007.
Leger et al. "Identification of CJC-1131-albumin bioconjugate as a stable and bioactive GLP-1(7-36) analog" *Bioorganic & Medicinal Chemistry Letters*, vol. 14, No. 17, pp. 4395-4398 (Sep. 2004).

* cited by examiner

*Primary Examiner* — David Lukton
(74) *Attorney, Agent, or Firm* — Nixon & Vanderhye P.C.

(57) ABSTRACT

The invention provides a compound of formula (I): X-PYY*(3-36) (I) wherein X is selected from H, $PYY_{1-2}$ (ie Tyr Pro) and D-Allo-Ue; PYY*(3-36) representing PYY (3-36) in which one or more residues is replaced by an acylated lysine group, the acyl group being selected from: $CO-C_{1-20}$ alkyl, $CO-C_{2-20}$ alkenyl, $CO-C_{5-10}$ aryl and $CO-C_{5-10}$ ar-$C_{1-20}$ alkyl; a variant or derivative thereof; or a salt or solvate thereof. The compounds are effective in inducing satiety and suppressing appetite and they are thus useful in treating various diseases, including obesity.

21 Claims, 10 Drawing Sheets

COMPOUNDS AND THEIR EFFECTS ON FEEDING BEHAVIOUR

Figure 1:
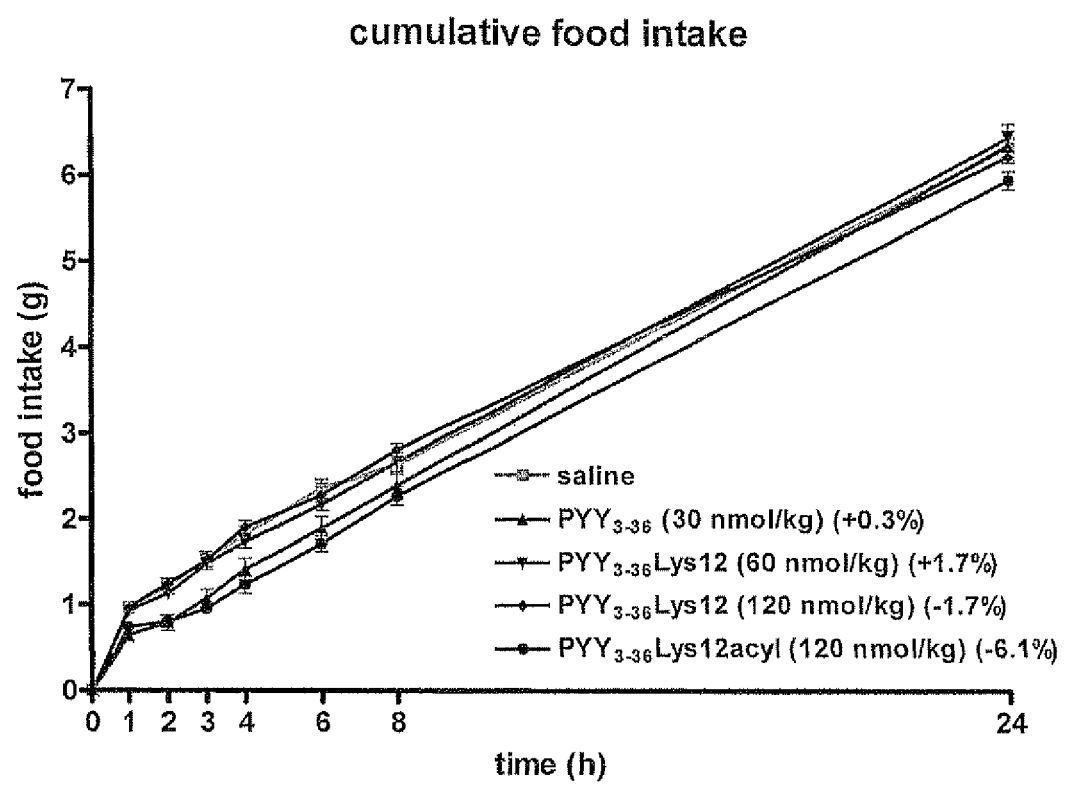

This application is the U.S. national phase under 35 U.S.C. 371 of International Application No. PCT/GB2007/002473 filed 03 Jul. 2007, which designated the U.S. and claims priority to Application No. GB 0613196.5 filed 03 Jul. 2006; the entire contents of each of which are hereby incorporated by reference.

1. FIELD OF THE INVENTION

This application relates to the use of agents to control appetite, feeding, food intake, energy expenditure and calorie intake, particularly in the field of obesity.

2. BACKGROUND OF THE INVENTION

According to the National Health and Nutrition Examination Survey (NHANES III, 1988 to 1994), between one third and one half of men and women in the United States are overweight. In the United States, sixty percent of men and fifty-one percent of women, of the age of 20 or older, are either overweight or obese. In addition, a large percentage of children in the United States are overweight or obese.

The cause of obesity is complex and multi-factorial. Increasing evidence suggests that obesity is not a simple problem of self-control but is a complex disorder involving appetite regulation and energy metabolism. In addition, obesity is associated with a variety of conditions associated with increased morbidity and mortality in a population. Although the etiology of obesity is not definitively established, genetic, metabolic, biochemical, cultural and psychosocial factors are believed to contribute. In general, obesity has been described as a condition in which excess body fat puts an individual at a health risk.

There is strong evidence that obesity is associated with increased morbidity and mortality. Disease risk, such as cardiovascular disease risk and type 2 diabetes disease risk, increases independently with increased body mass index (BMI). Indeed, this risk has been quantified as a five percent increase in the risk of cardiac disease for females, and a seven percent increase in the risk of cardiac disease for males, for each point of a BMI greater than 24.9 (see Kenchaiah et al., *N. Engl. J. Med.* 347:305, 2002; Massie, *N. Engl. J. Med.* 347: 358, 2002). In addition, there is substantial evidence that weight loss in obese persons reduces important disease risk factors. Even a small weight loss, such as 10% of the initial body weight in both overweight and obese adults has been associated with a decrease in risk factors such as hypertension, hyperlipidemia, and hyperglycemia.

Although diet and exercise provide a simple process to decrease weight gain, overweight and obese individuals often cannot sufficiently control these factors to effectively lose weight. Pharmacotherapy is available; several weight loss drugs have been approved by the Food and Drug Administration that can be used as part of a comprehensive weight loss program. However, many of these drugs have serious adverse side effects. When less invasive methods have failed, and the patient is at high risk for obesity related morbidity or mortality, weight loss surgery is an option in carefully selected patients with clinically severe obesity. However, these treatments are high-risk, and suitable for use in only a limited number of patients. It is not only obese subjects who wish to lose weight. People with weight within the recommended range, for example, in the upper part of the recommended range, may wish to reduce their weight, to bring it closer to the ideal weight. Thus, a need remains for agents that can be used to effect weight loss in overweight and obese subjects.

In WO03/026591, it is disclosed that peripheral administration of peptide YY (hereinafter PYY), or an agonist thereof, to a subject results in decreased food intake, caloric intake, and appetite, and an alteration in energy metabolism. It is disclosed that the PYY or agonist thereof is preferably an N-terminally deleted PYY molecule $PYY_{3-36}$.

3. SUMMARY OF THE INVENTION

The present invention provides a compound of formula (I):

$$X\text{-}PYY^*(3\text{-}36) \qquad (I)$$

Wherein X is selected from H, $PYY_{1-2}$ (ie Tyr Pro) and D-Allo-Ile;

PYY*(3-36) representing PYY (3-36) in which one or more residues is replaced by an acylated lysine group, the acyl group being selected from: $CO\text{—}C_{1\text{-}20}$ alkyl, $CO\text{—}C_{2\text{-}20}$ alkenyl, $CO\text{—}C_{5\text{-}10}$ aryl and $CO\text{—}C_{5\text{-}10}$ ar-$C_{1\text{-}20}$ alkyl;

a variant or derivative thereof; or a salt or solvate thereof.

The present invention also provides a compound of formula (Ia):

$$X\text{-}PYY^*(3\text{-}36) \qquad (Ia)$$

PYY (3-36) being:

```
                                            SEQ ID NO: 2
3   4   5   6   7   8   9   10  11  12  13  14
Ile Lys Pro Glu Ala Pro Gly Glu Asp Ala Ser Pro 15  16  17  18  19  20  21  22  23  24  25  26
Glu Glu Leu Asn Arg Tyr Tyr Ala Ser Leu Arg His 27  28  29  30  31  32  33  34  35  36
Tyr Leu Asn Leu Val Thr Arg Gln Arg Tyr
```

Wherein X is selected from H, $PYY_{1-2}$ (ie Tyr Pro) and D-Allo-Ile.

PYY*(3-36) representing PYY (3-36) in which one or more of residues:

3-Ile

7-Ala

9-Gly

12-Ala

17-Leu

22-Ala

24-Leu

28-Leu is replaced by a residue (II):

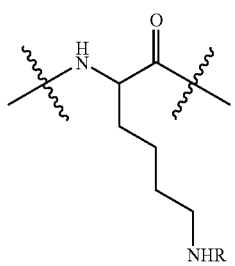

(II)

wherein R is selected from CO—$C_{1-20}$ alkyl, CO—$C_{2-20}$ alkenyl, CO—$C_{5-10}$ aryl and CO—$C_{5-10}$ ar-$C_{1-20}$ alkyl;
a variant or derivative thereof; or a salt or solvate thereof.

The invention also provides uses of a compound of formula (I), methods that use a compound of formula (I), compositions comprising a compound of formula (I), and methods of making a compound of formula (I).

4. BRIEF DESCRIPTION OF THE FIGURES

FIG. 1 shows the results of an experiment in which the appetite suppressing effects in mice of a compound of the invention were compared with native PYY(3-36) (SEQ ID NO:2), a further analogue of PYY(3-36) and saline.

Figure 2:
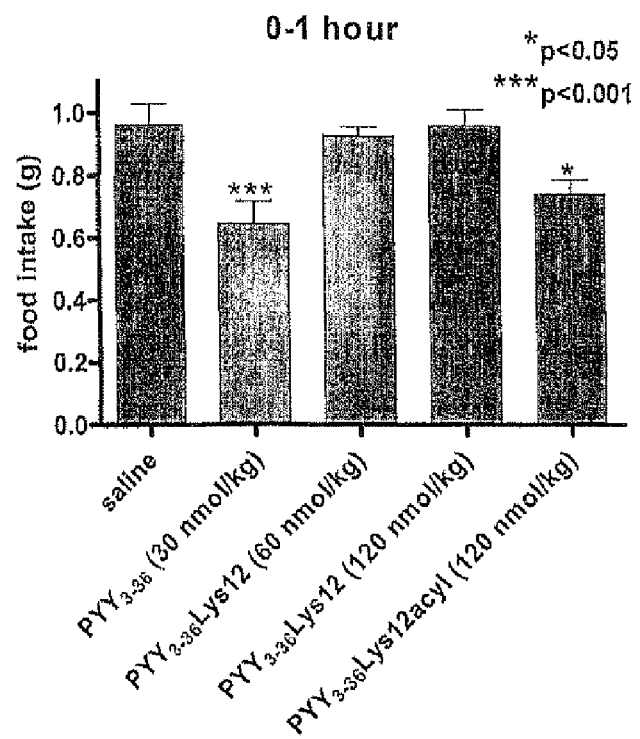
Figure 2:
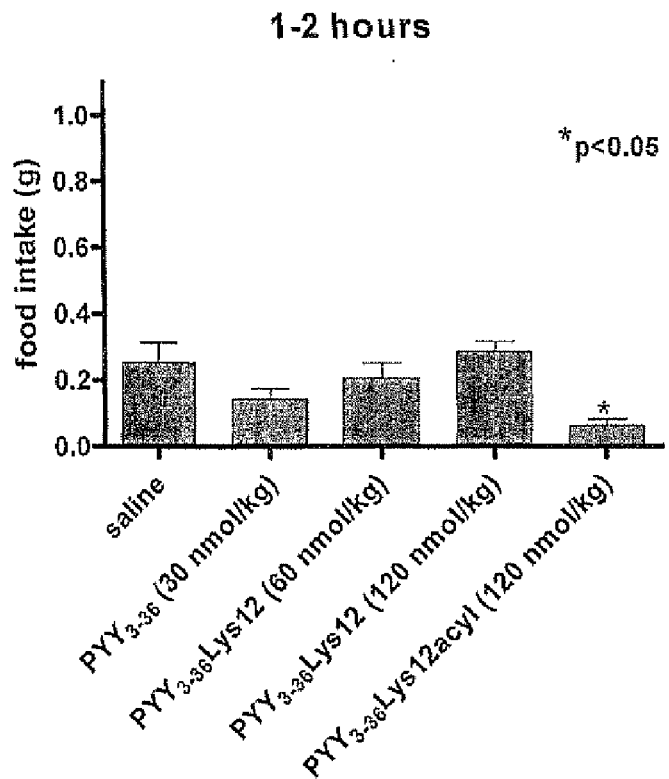
Figure 2:
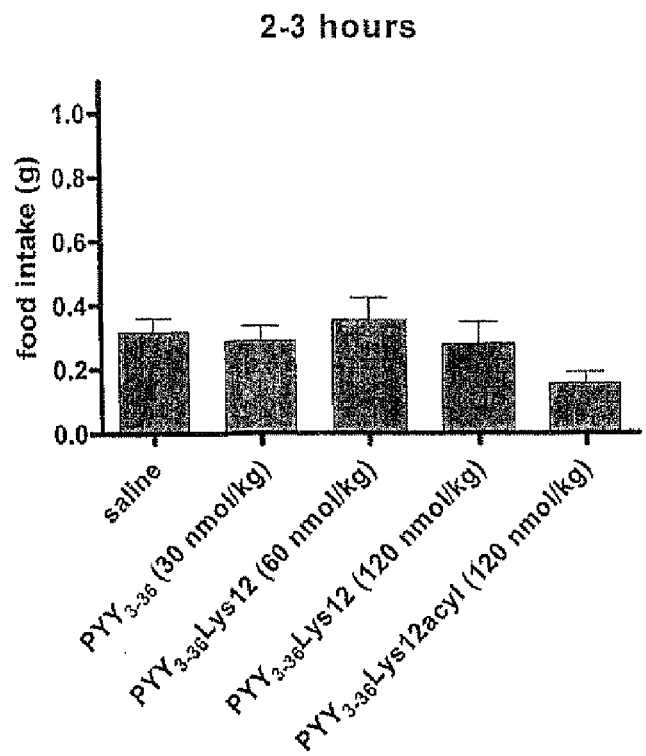
Figure 2:
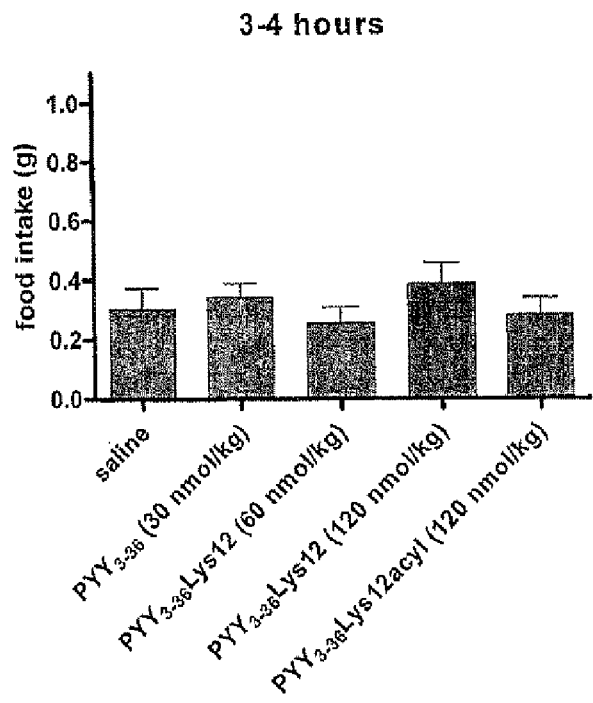
Figure 2:
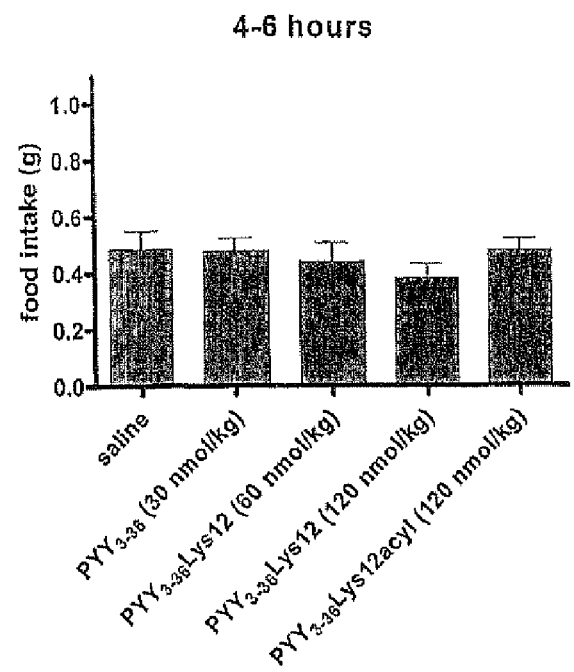
Figure 2:
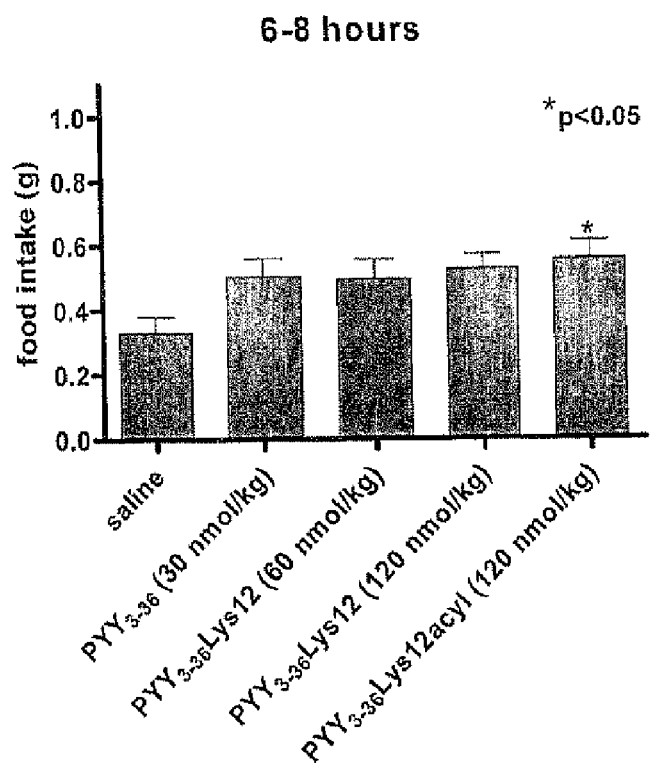
Figure 2:
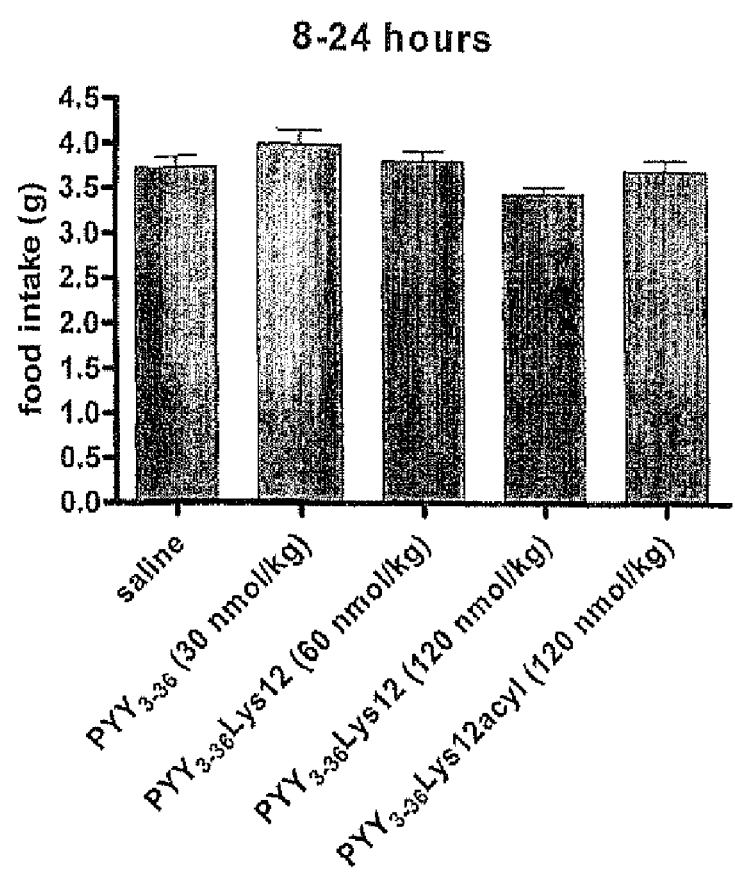

FIGS. 2 a) to 2 g) show the results of the experiment of FIG. 1 broken down by time interval.

Figure 3:
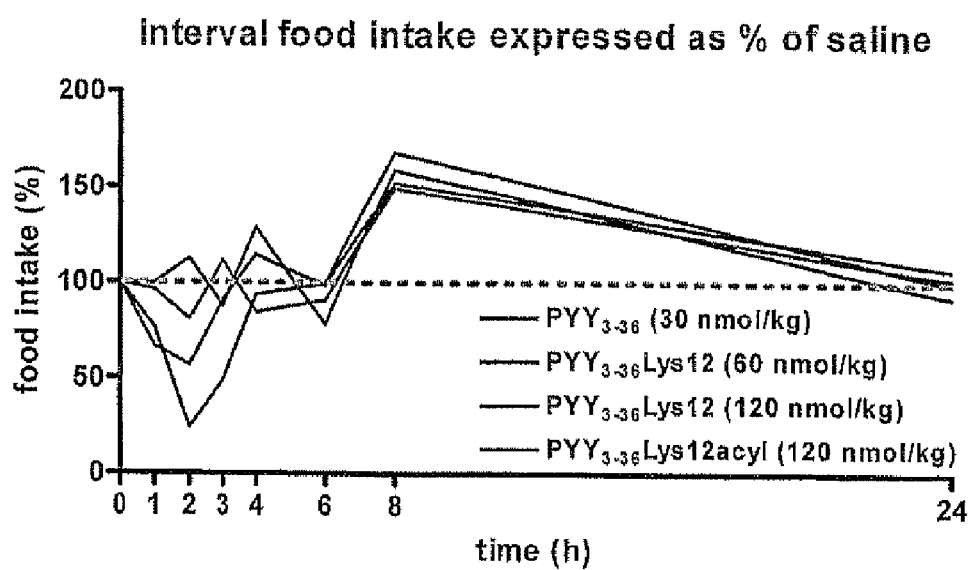

FIG. 3 shows the results of the experiment of FIG. 1 expressed as a % of saline.

Figure 4:
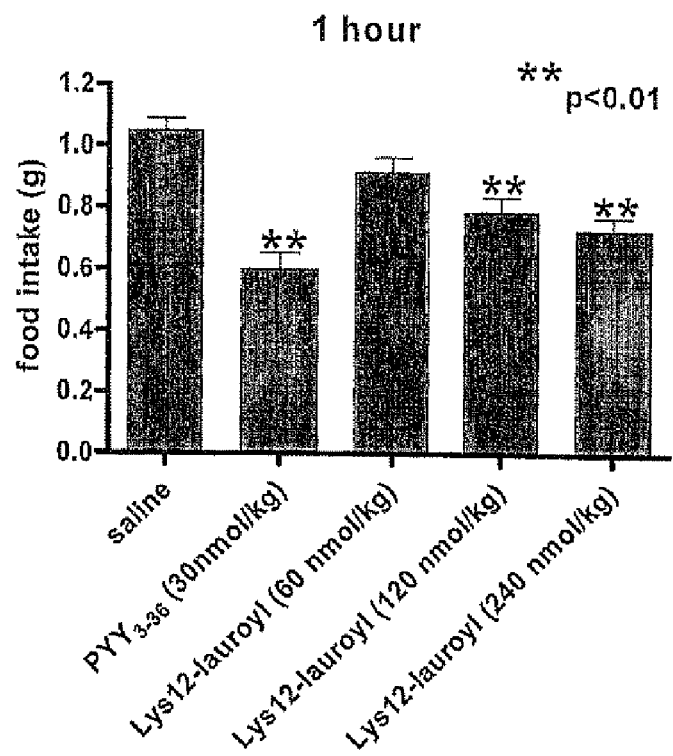
Figure 4:
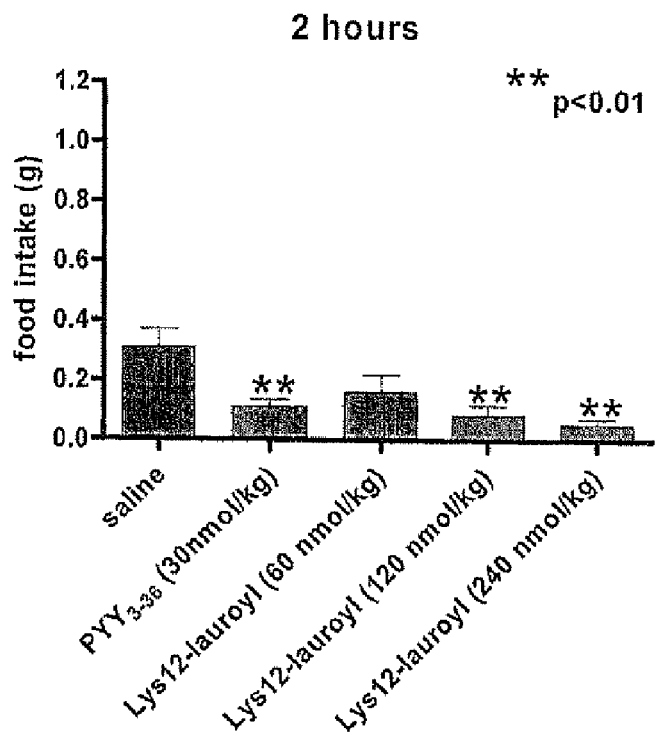
Figure 4:
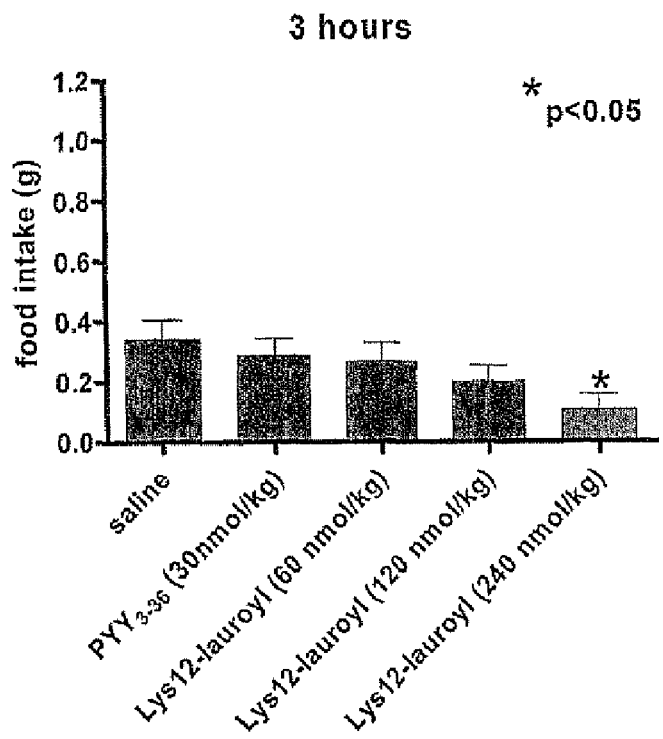
Figure 4:
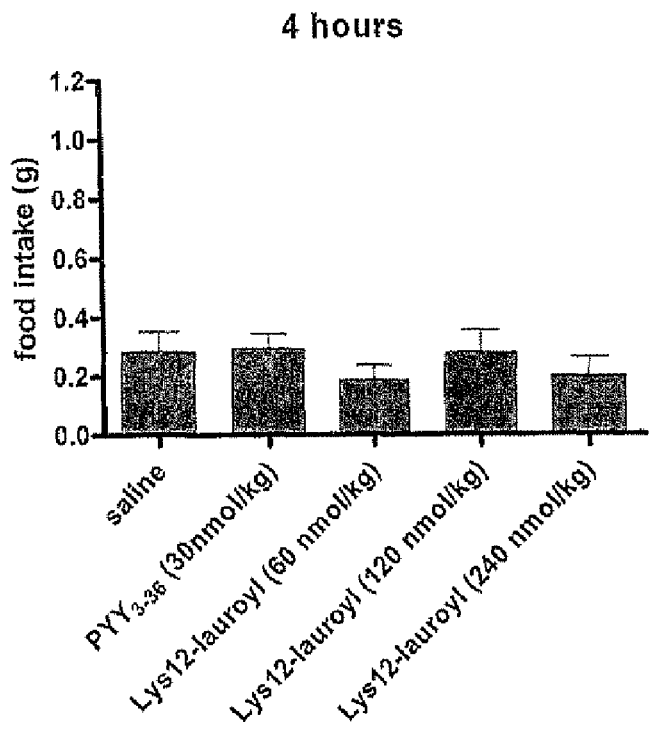
Figure 4:
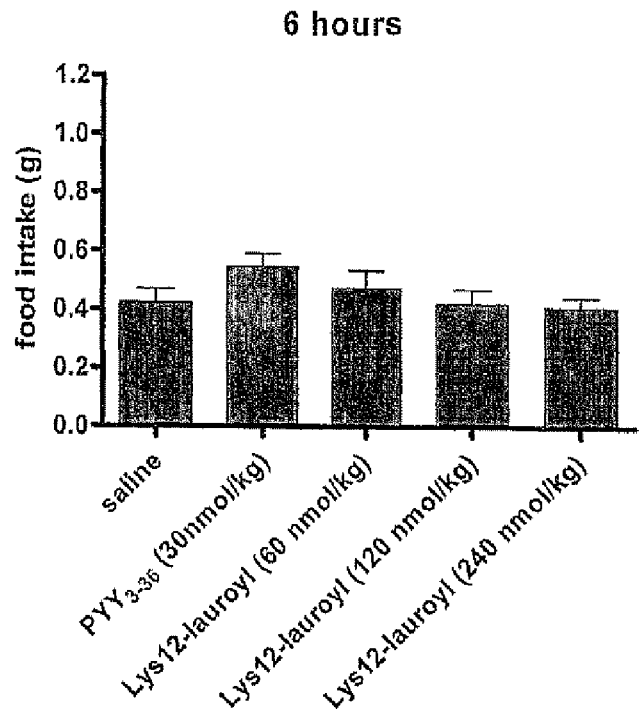
Figure 4:
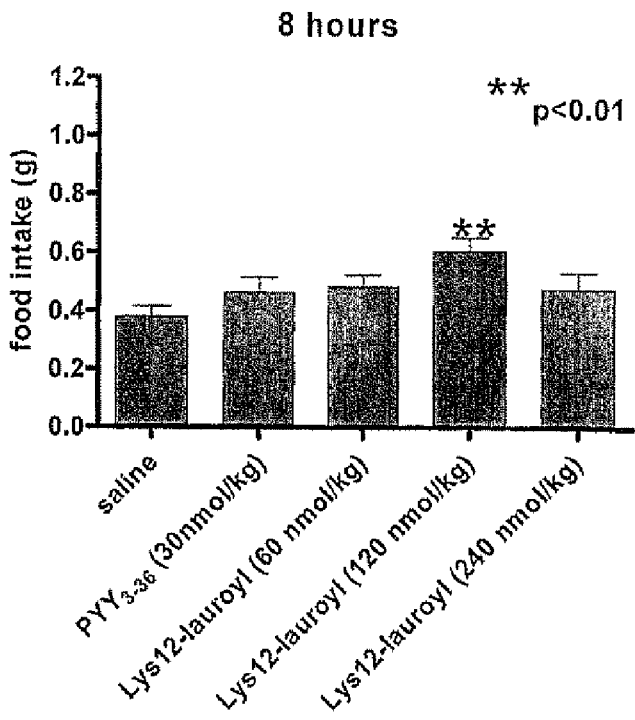
Figure 4:
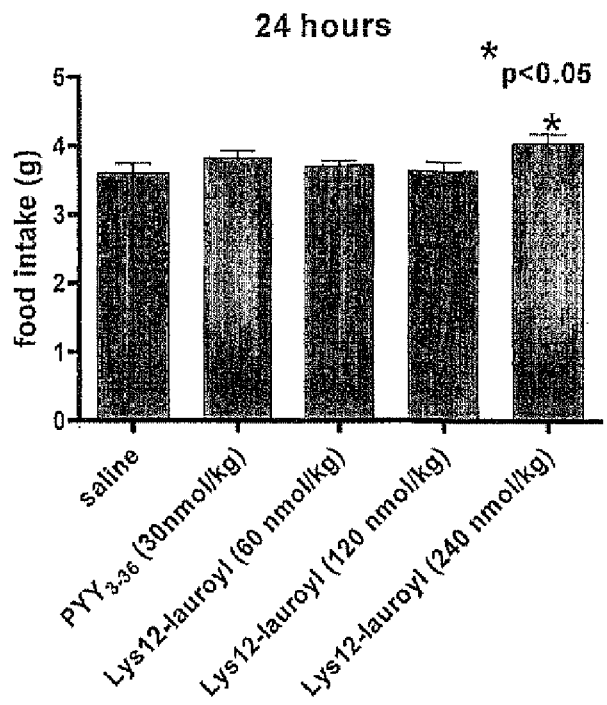

FIGS. 4 a) to 4 g) show the results of an experiment which the appetite suppressing effects in mice of a compound of the invention at various dosages were compared with native PYY (3-36) and saline.

Figure 5:
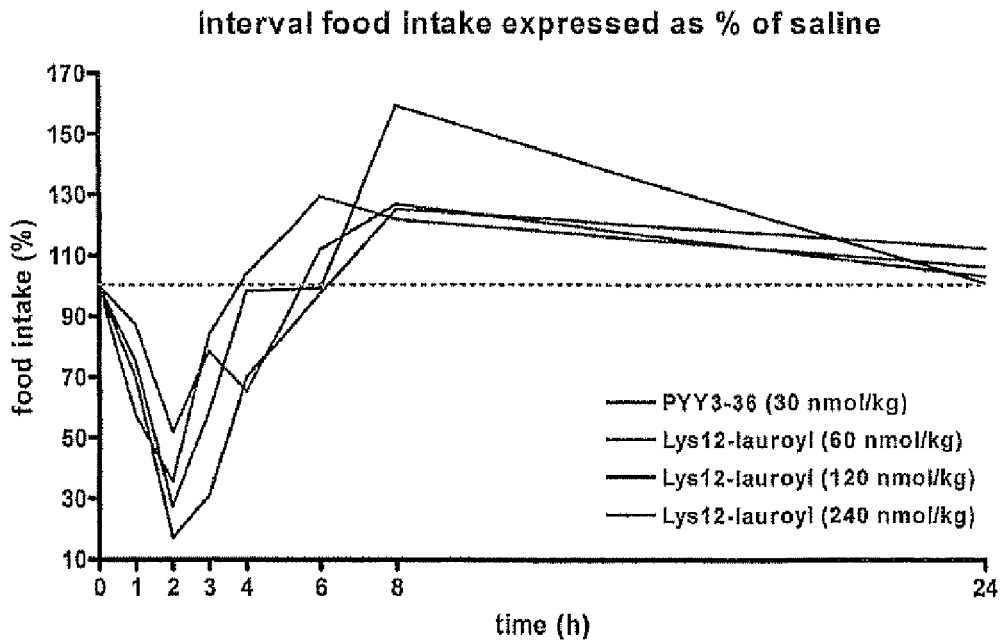

FIG. 5 shows the results of the experiment of FIG. 4 expressed as a % of saline.

5. SEQUENCE LISTING

The amino acid sequences listed in the application are shown using standard letter abbreviations for amino acids.

6. DEFINITIONS

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Appetite: A natural desire, or longing for food. In one embodiment, appetite is measured by a survey to assess the desire for food. Increased appetite generally leads to increased feeding behavior.

Appetite Suppressants Compounds that decrease the desire for food. Commercially available appetite suppressants include, but are not limited to, amfepramone (diethylpropion), phentermine, mazindol and phenylpropanolamine fenfluramine, dexfenfluramine, and fluoxetine.

Body Mass Index (BMI): A mathematical formula for measuring body mass, also sometimes called Quetelet's Index. BMI is calculated by dividing weight (in kg) by height$^2$ (in meters$^2$). The current standards for both men and women accepted as "normal" are a BMI of 20-24.9 kg/m$^2$. In one embodiment, a BMI of greater than 25 kg/m$^2$ can be used to identify an obese subject. Grade I obesity corresponds to a BMI of 25-29.9 kg/m$^2$. Grade II obesity corresponds to a BMI of 30-40 kg/m$^2$; and Grade III obesity corresponds to a BMI greater than 40 kg/m$^2$ (Jequier, Am. J Clin. Nutr. 45:1035-47, 1987). Ideal body weight will vary among species and individuals based on height, body build, bone structure, and sex.

Conservative substitutions: The replacement of an amino acid residue by another, biologically similar residue in a polypeptide. The term "conservative variation" also includes the use of a substituted amino acid, i.e. an amino with one or more atoms replaced with another atom or group, in place of a parent amino acid provided that antibodies raised to the substituted polypeptide also immunoreact with the unsubstituted polypeptide.

Diabetes: A failure of cells to transport endogenous glucose across their membranes either because of an endogenous deficiency of insulin and/or a defect in insulin sensitivity. Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type I) and non-insulin dependent diabetes mellitus (NIDDM, type II) which differ in etiology, pathology, genetics, age of onset, and treatment.

The two major forms of diabetes are both characterized by an inability to deliver insulin in an amount and with the precise timing that is needed for control of glucose homeostasis. Diabetes type I, or insulin dependent diabetes mellitus (IDDM) is caused by the destruction of β cells, which results in insufficient levels of endogenous insulin. Diabetes type II, or non-insulin dependent diabetes, results from a defect in both the body's sensitivity to insulin, and a relative deficiency in insulin production.

Food intake: The amount of food consumed by an individual. Food intake can be measured by volume or by weight. For example, food intake may be the total amount of food consumed by an individual. Or, food intake may be the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

Hyperpolarization: A decrease in the membrane potential of a cell. Inhibitory neurotransmitters inhibit the transmission of nerve impulses via hyperpolarization. This hyperpolarization is called an inhibitory postsynaptic potential (IPSP). Although the threshold voltage of the cell is unchanged, a hyperpolarized cell requires a stronger excitatory stimulus to reach threshold.

Normal Daily Diet: The average food intake for an individual of a given species. A normal daily diet can be expressed in terms of caloric intake, protein intake, carbohydrate intake, and/or fat intake. A normal daily diet in humans generally comprises the following: about 2,000, about 2,400, or about 2,800 to significantly more calories. In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake. One of skill in the art can readily identify the normal daily diet of an individual of any species.

Obesity: A condition in which excess body fat may put a person at health risk (see Barlow and Dietz, *Pediatrics* 102:E29, 1998; National Institutes of Health, National Heart, Lung, and Blood Institute (NHLBI), *Obes. Res.* 6 (suppl. 2):51S-209S, 1998). Excess body fat is a result of an imbalance of energy intake and energy expenditure. For example, the Body Mass Index (BMI) may be used to assess obesity. In one commonly used convention, a BMI of 25.0 kg/m² to 29.9 kg/m² is overweight, while a BMI of 30 kg/m² is obese.

In another convention, waist circumference is used to assess obesity. In this convention, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Fam. Phys.* 63:2185, 2001).

Overweight: An individual who weighs more than their ideal body weight. An overweight individual can be obese, but is not necessarily obese. For example, an overweight individual is any individual who desires to decrease their weight. In one convention, an overweight individual is an individual with a BMI of 25.0 kg/m² to 29.9 kg/m²

Pegylated and pegylation: the process of reacting a poly(alkylene glycol), preferably an activated poly(alkylene glycol) to form a covalent bond. A facilitator may be used, for example an amino acid, e.g. lysine. Although "pegylation" is often carried out using poly(ethylene glycol) or derivatives thereof, such as methoxy poly(ethylene glycol), the term is not limited herein to the use of methoxy poly(ethylene glycol) but also includes the use of any other useful poly(alkylene glycol), for example poly(propylene glycol).

Peptide YY (PYY): The term PYY as used herein refers to a peptide YY polypeptide, a hormone secreted into the blood by cells lining the lower small intestine (the ileum) and the colon.

Peripheral Administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein encompass any amino acid sequence and include modified sequences such as glycoproteins. The term "polypeptide" is specifically covers naturally occurring proteins, as well as those which are recombinantly or synthetically produced. The term "polypeptide fragment" refers to a portion of a polypeptide, for example a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest has been fused to another peptide that does not decrease its desired activity.

Therapeutically effective amount: A dose sufficient to prevent advancement, or to cause regression of a disorder, or which is capable of relieving a sign or symptom of a disorder, or which is capable of achieving a desired result. In several embodiments, a therapeutically effective amount of a compound of the invention is an amount sufficient to inhibit or halt weight gain, or an amount sufficient to decrease appetite, or an amount sufficient to reduce caloric intake or food intake or increase energy expenditure.

7. DETAILED DESCRIPTION

As mentioned above, the invention provides a compound of formula (I):

X-PYY*(3-36)                                         (I)

wherein X is selected from H, $PYY_{1-2}$ (ie Tyr Pro) and D-Allo-Ile;

PYY*(3-36) representing PYY (3-36) (SEQ ID NO:2) in which one or more residues is replaced by an acylated lysine group, the acyl group being selected from: CO—$C_{1-20}$ alkyl, CO—$C_{2-20}$ alkenyl, CO—$C_{5-10}$ aryl and CO—$C_{5-10}$ ar-$C_{1-20}$ alkyl;

a variant or derivative thereof; or a salt or solvate thereof.

In particular, the residue or residues that are replaced are selected from the neutral, non-cyclic residues. Preferably, the residue or residues that are replaced are selected from the neutral, non-cyclic residues and are not proline residues. Preferred residues to be substituted include Alanine, Leucine, Isoleucine and Glycine, in particular Alanine. Preferably, one, two or three residues are replaced by an acylated lysine group. Preferably, the replacement of the residue concerned does not significantly reduce the affinity of the PYY (3-36) molecule at the Y2 receptor. Binding at the Y2 receptor can be measured by standard methods.

In particular, the invention provides a compound of formula (Ia):

X-PYY*(3-36)                                         (Ia)

Wherein X is selected from H, $PYY_{1-2}$ (ie Tyr Pro) and D-Allo-Ile.

PYY*(3-36) representing PYY (3-36) (SEQ ID NO:2) in which one or more of residues:

```
3-Ile

7-Ala

9-Gly

12-Ala

17-Leu

22-Ala
```

24-Leu

28-Leu is replaced by a residue (II):

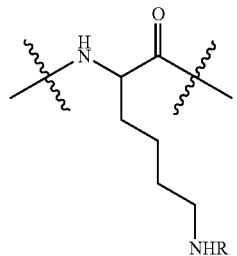

(II)

wherein R is selected from CO—$C_{1-20}$ alkyl, CO—$C_{2-20}$ alkenyl, CO—$C_{5-10}$aryl and CO—$C_{5-10}$-ar-$C_{1-20}$ alkyl;
a variant or derivative thereof; or a salt or solvate thereof.

The compounds of the invention as represented in formula (I) and (Ia) are related to $PYY_{3-36}$ and they have acyl side chains attached in a specific manner at particular locations in the molecule. Typically, the acyl groups are of the form $R_1CO—$, where $R_1$ can be a $C_{1-20}$ alkyl group, a $C_{2-20}$ alkenyl group, a $C_{5-10}$ aryl group or a $C_{5-10}$ ar-$C_{1-20}$ alkyl group. Particular $R_1$ alkyl groups include lauroyl, stearyl and palmityl, and particular alkenyl groups include oleyl.

The effects of administration of 240 nmol/kg $PYY_{3-36}$ $Lys_{12}$lauroyl ($PYY_{3-36}$ with the residue at position 12 replaced with a lysine residue coupled to a lauroyl group, SEQ ID NO: 14) and 60 nmol/kg $PYY_{3-36}$ to mice were investigated and it was found that the administration of 240 nmol/kg $PYY_{3-36}Lys_{12}$lauroyl resulted in a slower onset of food intake reduction than that seen with 60 nmol/kg of the native $PYY_{3-36}$ but that the administration of 240 nmol/kg $PYY_{3-36}Lys_{12}$lauroyl showed greater persistence of effect when compared with the administration of 60 nmol/kg of native $PYY_{3-36}$.

Increased duration of appetite suppression can be particularly important to avoid the effect known as "escape". A short duration appetite suppressant may reduce appetite for the time covered by one meal and, in that meal, the subject typically eats less food. If, however, the appetite suppressant is then metabolized or otherwise removed from the circulation of the subject, then by the time of the next mealtime, the subject can regain its "normal" appetite. In view of the subject having eaten a small meal at the previous mealtime, the subject may in fact have an increased appetite by the time of the second meal. If the subject satisfies that appetite, it is possible for the food intake over the two meals, in total, to be no lower than the food intake would have been without the appetite suppressant. That is to say that the subject may have "escaped" from the effects of the appetite suppressant. "Escape" can be reduced by using additional doses of appetite suppressant, or by using an appetite suppressant with a longer duration of action. If the subject has a reduced appetite for longer, then the degree to which it can make up the missed food from one meal in the next meal is reduced as there is a practical limit to the total capacity for food in a particular meal.

Furthermore, it has been found that prolonged continuous infusion of a short duration appetite suppressant is less effective than administration of a single dose of a longer acting appetite suppressant even if the level of the shorter acting suppressant is maintained in the bloodstream for a similar length of time as the longer acting suppressant by continuous dosing.

Preferably, the $PYY*_{3-36}$ is based on human $PYY_{3-36}$.

The human full length PYY polypeptide is shown in SEQ ID NO: 1; human $PYY_{3-36}$ is shown in SEQ ID NO: 2. The subscripts refer to the location on the full length PYY molecule in the species in question, beginning at the N-terminus. Thus $PYY_{3-36}$ is a peptide PYY molecule lacking amino acids 1 and 2 at the N-terminus. Analogous numbering is used for other fragments and variants of PYY described herein. Human $PYY_{3-36}$ is:

SEQ ID NO: 2

| 3 | 4 | 5 | 6 | 7 | 8 | 9 | 10 | 11 | 12 | 13 | 14 |
|---|---|---|---|---|---|---|----|----|----|----|----|
| Ile | Lys | Pro | Glu | Ala | Pro | Gly | Glu | Asp | Ala | Ser | Pro |

| 15 | 16 | 17 | 18 | 19 | 20 | 21 | 22 | 23 | 24 | 25 | 26 |
|----|----|----|----|----|----|----|----|----|----|----|----|
| Glu | Glu | Leu | Asn | Arg | Tyr | Tyr | Ala | Ser | Leu | Arg | His |

| 27 | 28 | 29 | 30 | 31 | 32 | 33 | 34 | 35 | 36 |
|----|----|----|----|----|----|----|----|----|----|
| Tyr | Leu | Asn | Leu | Val | Thr | Arg | Gln | Arg | Tyr |

Preferably, one, two or three residues are each replaced by a residue (II). One or two residues may each be replaced by a residue (II). For example, one residue is replaced by a residue (II).

In one embodiment of the invention, the residue or residues replaced are selected from 3-Ile, 7-Ala, 9-Gly, 12-Ala, 17-Leu, 22-Ala and 24-Leu; more preferably from 3-Ile, 7-Ala, 9-Gly, 12-Ala, 17-Leu and 22-Ala; particularly from 3-Ile, 7-Ala, 9-Gly, 12-Ala and 17-Leu, for example from 3-Ile, 7-Ala, 9-Gly and 12-Ala.

In another embodiment of the invention, the residues replaced are selected from 7-Ala, 12-Ala, and 22-Ala. More preferably, the residues replaced are selected from 7-Ala, 12-Ala, for example 12-Ala.

In one particular embodiment, the molecule of formula (I) is X-$PYY_{3-36}Lys_{12}$-Acyl, ie X-$PYY_{3-11}$-(Lys-Acyl)-$PYY_{13-36}$. $PYY_{3-11}$ refers to a portion of the human PYY molecule containing residues 3 to 11 and $PYY_{13-36}$ refers to a portion of the human PYY molecule containing residues 13 to 36. The human $PYY_{3-11}$ and the human $PYY_{13-36}$ sequences are shown as SEQ ID NO:11 and SEQ ID NO:12 respectively (see Table 2). $PYY_{3-36}Lys_{12}$ refers to a human PYY molecule which lacks amino acids 1 and 2 at the N terminus and where a lysine residue has been substituted for the Alanine at position 12. The sequence of $PYY_{3-36}Lys_{12}$ is shown as SEQ ID NO:13 in Table 2. $PYY_{3-36}Lys_{12}$-Acyl refers to a human PYY molecule which lacks amino acids 1 and 2 at the N terminus and where a Lysine residue with an acylated side chain has been substituted for the Alanine at position 12. The sequence of $PYY_{3-36}Lys_{12}$-Acyl is shown as SEQ ID NO:14 in Table 2. To reflect the fact that the Lysine side chain has been modified, the letter X is used to denote position 12 in $PYY_{3-36}Lys_{12}$-Acyl.

The $PYY_{3-36}$ portions in a molecule of the invention may be, or may be related to, a PYY from a species other than human. The sequence of PYYs of various species are included in Table 1 (SEQ ID NOS: 3 to 10), including e.g. rat and pig PYY. The $PYY_{3-36}$ portions in a molecule of the invention may also be taken from any of those sequences.

TABLE 1

PYY sequence of various species

PEPTIDE YY  AA SEQUENCE

Human       YPIKLPEAPGEDASPEELNRYYASLRHYLNLVTRQRY
            (SEQ ID NO: 1)

TABLE 1-continued

PYY sequence of various species

| PEPTIDE YY | AA SEQUENCE |
|---|---|
| Human 3-36 | IKPEAPGEDASPEELNRYYASLRHYLNLVTRQRY (SEQ ID NO: 2) |
| Rat | YPAKPEAPGEDASPEELSRYYASLRHYLNLVTRQRY (SEQ ID NO: 3) |
| Pig | YPAKPEAPGEDASPEELSRYYASLRHYLNLVTRQRY (SEQ ID NO: 4) |
| Guinea pig | YPSKPEAPGSDASPEELARYYASLRHYLNLVTRQRY (SEQ ID NO: 5) |
| Frog | YPPKPENPGEDASPEEMTKYLTALRHYINLVTRQRY (SEQ ID NO: 6) |
| Raja | YPPKPENPGDDAAPEELAKYYSALRHYINLITRQRY (SEQ ID NO: 7) |
| Dogfish | YPPKPENPGEDAPPEELAKYYSALRHYINLITRQRY (SEQ ID NO: 8) |
| Lampetra | FPPKPDNPGDNASPEQMARYKAAVRHYINLITRQRY (SEQ ID NO: 9) |
| Petromyzon | MPPKPDNPSPDASPEELSKYMLAVRNYINLITRQRY (SEQ ID NO: 10) |

TABLE 2

PYY sequences of the present invention, or discussed in the context of the present invention:

| | |
|---|---|
| $PYY_{3-11}$ | IKPEAPGED (SEQ ID NO: 11) |
| $PYY_{13-36}$ | SPEELNRYYASLRHYLNLVTRQRY (SEQ ID NO: 12) |
| $PYY_{3-36}Lys12$ | IKPEAPGEDKSPEELNRYYASLRHYLNLVTRQRY (SEQ ID NO: 13) |
| $PYY_{3-36}ModLys12$ | IKPEAPGEDXSPEELNRYYASLRHYLNLVTRQRY (SEQ ID NO: 14) |

In a similar manner to native PYY and $PYY_{3-36}$, the compounds of the invention are typically selective for the Y2 receptor. That is, they bind with higher affinity to Y2 compared to other receptors, such as Y1, Y3, Y4, Y5 and Y6. These receptors are recognized based on binding affinities, pharmacology, and sequence (if known). Most, if not all of these receptors are G protein coupled receptors. The Y1 receptor is generally considered to be postsynaptic and mediates many of the known actions of neuropeptide Y in the periphery. Originally, this receptor was described as having poor affinity for C-terminal fragments of neuropeptide Y, such as the 13-36 fragment, but interacts with the full length neuropeptide Y and peptide YY with equal affinity (e.g., see PCT publication WO 93/09227).

Pharmacologically, the Y2 receptor is distinguished from Y1 by exhibiting affinity for C-terminal fragments of neuropeptide Y. The Y2 receptor is most often differentiated by the affinity of neuropeptide Y(13-36), although the 3-36 fragment of neuropeptide Y and peptide YY provides improved affinity and selectivity (see Dumont et al., *Society for Neuroscience Abstracts* 19:726, 1993). Signal transmission through both the Y1 and the Y2 receptors are coupled to the inhibition of adenylate cyclase. Binding to the Y2 receptor was also found to reduce the intracellular levels of calcium in the synapse by selective inhibition of N-type calcium channels. In addition, the Y2 receptor, like the Y1 receptors, exhibits differential coupling to second messengers (see U.S. Pat. No. 6,355,478). Y2 receptors are found in a variety of brain regions, including the hippocampus, substantia nigra-lateralis, thalamus, hypothalamus, and brainstem. The human, murine, monkey and rat Y2 receptors have been cloned (e.g., see U.S. Pat. Nos. 6,420,352 and 6,355,478).

Binding to the Y2 receptor can be assessed by standard techniques. For example, an ELISA or fluorescence-based assay may be used to assess binding of a compound at the receptor. A cell-based functional assay can be used to assess whether a compound is an agonist or an antagonist of the receptor.

The mechanism by which the Acylated lysine side chain brings about its advantageous effects is not known. It is possible that its lipophilic nature causes the moiety to bind with albumin and thus brings about a reduced rate of clearance from a subject thus increasing half life and duration of effect.

Whilst the acyl side chains may be lower acyl, for example $C_1$-$C_9$ acyl, especially $C_{1-6}$ acyl, they are preferred to be $C_{4-40}$, in particular $C_{8-25}$ acyl, especially $C_{16}$ or $C_{18}$ acyl. Lauroyl is especially preferred as an acyl side chain as is palmityl. The acyl substituent is attached to the lysine residue in such a way that a carboxyl group of the acyl substituent forms an amide bond with an amino group of the lysine residue.

Variants:

The $PYY_{3-36}$ portions of the molecule may be variants of the equivalent native portions, for example the $PYY_{3-36}$ portions may be variants of the equivalent native human portions. Variants include $PYY_{3-36}$ portions with deletions, insertions, inversions, repeats and substitutions, (e.g., conservative substitutions and non-conservative substitutions; see, e.g., Table 3 below) which retain at least some of the activity of a corresponding non-variant molecule when in a molecule of the invention. More than one amino acid (e.g., 2, 3 or 4) can be deleted or inserted or substituted with another amino acid. Accordingly, the $PYY_{3-36}$ portions as present in a compound of formula (I) preferably include at least 29 amino acids of the native sequence of the $PYY_{3-36}$ portion. Preferably, the C-terminal six amino acids of native $PYY_{3-36}$ are all present in a molecule of the invention.

Typically conservative substitutions are the replacements, for one another, among the aliphatic amino acids Ala, Val, Leu and Ile; interchange of Ser and Thr containing hydroxy residues, interchange of the acidic residues Asp and Glu, interchange between the amide residues Asn and Gln, interchange of the basic residues Lys and Arg, interchange of the aromatic residues Phe and Tyr, and interchange of the small-sized amino acids Ala, Ser, Thr, Met and Gly. Guidance concerning how to make phenotypically silent amino acid substitutions, ie substitutions that do not alter the expressed phenotype, is provided in Bowie et al., *Science* 247:1306-1310, 1990.

TABLE 3

Non-limiting examples of conservative amino acid substitutions

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |

TABLE 3-continued

Non-limiting examples of conservative amino acid substitutions

| Original Residue | Conservative Substitutions |
| --- | --- |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variants of the $PYY_{3-36}$ portion further include variants in which one or more amino acids (for example 2, 3 or 4) of the $PYY_{3-36}$ of one species are substituted by an amino acid present at the equivalent position in PYY derived from a different species. The sequences of PYYs of various species are included in Table 1 above. In particular, the $PYY_{3-36}$ portions of the molecule which comprise the human PYY sequence may be substituted by one or more amino acids (for example 2, 3 or 4) which are present at the equivalent position in PYY derived from a different species.

Derivatives

A compound of the invention may comprise the structure of formula (I) modified by well known processes including amidation, glycosylation, carbamylation, acylation, for example acetylation, sulfation, phosphylation, cyclization, lipidization and pegylation. The structure of formula (I) may be modified at random positions within the molecule, or at predetermined positions within the molecule and may include one, two, three or more attached chemical moieties.

A compound of the invention may be a fusion protein, whereby the structure of formula (I) is fused to another protein or polypeptide (the fusion partner) using recombinant methods known in the art. Alternatively, such a fusion protein may be synthetically synthesized by any known method. Such a fusion protein comprises the structure of formula (I). Any suitable peptide or protein can be used as the fusion partner (e.g., serum albumin, carbonic anhydrase, glutathione-S-transferase or thioredoxin, etc.). Preferred fusion partners will not have an adverse biological activity in vivo. Such fusion proteins may be made by linking the carboxy-terminus of the fusion partner to the amino-terminus of the structure of formula (I) or vice versa. Optionally, a cleavable linker may be used to link the structure of formula (I) to the fusion partner. A resulting cleavable fusion protein may be cleaved in vivo such that an active form of a compound of the invention is released. Examples of such cleavable linkers include, but are not limited to, the linkers D-D-D-D-Y, G-P-R, A-G-G and H-P-F-H-L, which can be cleaved by enterokinase, thrombin, ubiquitin cleaving enzyme and renin, respectively. See, e.g., U.S. Pat. No. 6,410,707.

A compound of the invention may be a physiologically functional derivative of the structure of formula (I). The term "physiologically functional derivative" is used herein to denote a chemical derivative of a compound of formula (I) having the same physiological function as the corresponding unmodified compound of formula (I). For example, a physiologically functionally derivative may be convertible in the body to a compound of formula (I). According to the present invention, examples of physiologically functional derivatives include esters, amides, and carbamates; preferably esters and amides.

Pharmaceutically acceptable esters and amides of the compounds of the invention may comprise a $C_{1-20}$ alkyl-, $C_{2-20}$ alkenyl-, $C_{5-10}$ aryl-, $C_{5-10}$ ar-$C_{1-20}$ alkyl-, or amino acid-ester or -amide attached at an appropriate site, for example at an acid group. Examples of suitable moieties are hydrophobic substituents with 4 to 26 carbon atoms, preferably 5 to 19 carbon atoms. Suitable lipid groups include, but are not limited to, the following: lauroyl ($C_{12}H_{23}$), palmityl ($C_{15}H_{31}$), oleyl ($C_{15}H_{29}$), stearyl ($C_{17}H_{35}$), cholate; and deoxycholate.

Methods for lipidization of sulfhydryl-containing compounds with fatty acid derivatives are disclosed in U.S. Pat. Nos. 5,936,092; 6,093,692; and 6,225,445. Fatty acid derivatives of a compound of the invention comprising a compound of the invention linked to fatty acid via a disulfide linkage may be used for delivery of a compound of the invention to neuronal cells and tissues. Lipidisation markedly increases the absorption of the compounds relative to the rate of absorption of the corresponding unlipidised compounds, as well as prolonging blood and tissue retention of the compounds. Moreover, the disulfide linkage in lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include, but are not limited to, the following: palmityl ($C_{15}H_{31}$,), oleyl ($C_{15}H_{29}$), stearyl ($C_{17}H_{35}$), cholate; and deoxycholate.

Cyclization methods include cyclization through the formation of a disulfide bridge and head-to-tail cyclization using a cyclization resin. Cyclized peptides may have enhanced stability, including increased resistance to enzymatic degradation, as a result of their conformational constraints. Cyclization may in particular be expedient where the uncyclized peptide includes an N-terminal cysteine group. Suitable cyclized peptides include monomeric and dimeric head-to-tail cyclized structures. Cyclized peptides may include one or more additional residues, especially an additional cysteine incorporated for the purpose of formation of a disulfide bond or a side chain incorporated for the purpose of resin-based cyclization.

A compound of the invention may be a pegylated structure of formula (I). Pegylated compounds of the invention may provide additional advantages such as increased solubility, stability and circulating time of the polypeptide, or decreased immunogenicity (see U.S. Pat. No. 4,179,337).

Chemical moieties for derivitization of a compound of the invention may also be selected from water soluble polymers such as polyethylene glycol, ethylene glycol/propylene glycol copolymers, carboxymethylcellulose, dextran, polyvinyl alcohol and the like. A polymer moiety for derivatisation of a compound of the invention may be of any molecular weight, and may be branched or unbranched. For ease in handling and manufacturing, the preferred molecular weight of a polyethylene glycol for derivatisation of a compound of the invention is from about 1 kDa to about 100 kDa, the term "about" indicating that in preparations of polyethylene glycol, some molecules will weigh more, some less, than the stated molecular weight. Polymers of other molecular weights may be used, depending on the desired therapeutic profile, for example the duration of sustained release desired, the effects, if any on biological activity, the ease in handling, the degree or lack of antigenicity and other known effects of the polyethylene glycol to a therapeutic protein or analog. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

Salts and solvates of compounds of the invention that are suitable for use in a medicament are those wherein a counterion or associated solvent is pharmaceutically acceptable.

However, salts and solvates having non-pharmaceutically acceptable counterions or associated solvents are within the scope of the present invention, for example, for use as intermediates in the preparation of the compounds of formula (I) and their pharmaceutically acceptable salts or solvates.

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycollic, lactic, salicylic, oxaloacetic, methanesulfonic, ethanesulfonic, p-toluenesulfonic, formic, benzoic, malonic, naphthalene-2-sulfonic, benzenesulfonic, and isethionic acids. Other acids such as oxalic, while not in themselves pharmaceutically acceptable, may be useful as intermediates in obtaining the compounds of the invention and their pharmaceutical acceptable salts. Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Those skilled in the art of organic chemistry will appreciate that many organic compounds can form complexes with solvents in which they are reacted or from which they are precipitated or crystallized. Such complexes are known as "solvates". For example, a complex with water is known as a "hydrate". The present invention provides solvates of compounds of the invention.

Conditions:

The invention provides a pharmaceutical composition comprising a compound of formula (I). The invention further provides the compound of formula (I) for use as a medicament.

The invention also provides a compound of formula (I) for use in the treatment of obesity or diabetes. The invention further provides a compound of formula (I) for use in reduction of appetite in a subject, for use in reduction of food intake in a subject, or for use in reduction of calorie intake in a subject.

The invention further provides the use of a compound of formula (I) for the manufacture of a medicament for the treatment of obesity or diabetes. The invention also provides the use of a compound of formula (I) for the manufacture of a medicament for reducing appetite in a subject, reducing food intake in a subject, or reducing calorie intake in a subject.

The invention further provides a method of treating obesity or diabetes in a subject in need thereof comprising administering to the subject an effective amount of a compound of formula (I). The invention also provides a method of reducing appetite in a subject, reducing food intake in a subject, or reducing calorie intake in a subject, comprising administering to the subject an effective amount of a compound of formula (I).

The subject to whom the compound is administered may be overweight, for example, obese. Alternatively, or in addition, the subject may be diabetic, for example having insulin resistance or glucose intolerance, or both. The subject may have diabetes mellitus, for example, the subject may have Type II diabetes. The subject may be overweight, for example, obese and have diabetes mellitus, for example, Type II diabetes.

In addition, or alternatively, the subject may have, or may be at risk of having, a disorder in which obesity or being overweight is a risk factor. Such disorders include, but are not limited to, cardiovascular disease, for example hypertension, atherosclerosis, congestive heart failure, and dyslipidemia; stroke; gallbladder disease; osteoarthritis; sleep apnea; reproductive disorders for example, polycystic ovarian syndrome; cancers, for example breast, prostate, colon, endometrial, kidney, and esophagus cancer; varicose veins; acnthosis nigricans; eczema; exercise intolerance; insulin resistance; hypertension hypercholesterolemia; cholithiasis; osteoarthritis; orthopedic injury; insulin resistance, for example, type 2 diabetes and syndrome X; and thromboembolic disease (see Kopelman, Nature 404:635-43; Rissanen et al., British Med. J. 301, 835, 1990).

Other disorders associated with obesity include depression, anxiety, panic attacks, migraine headaches, PMS, chronic pain states, fibromyalgia, insomnia, impulsivity, obsessive compulsive disorder, and myoclonus. Furthermore, obesity is a recognized risk factor for increased incidence of complications of general anesthesia. (See e.g., Kopelman, Nature 404:635-43, 2000). In general, obesity reduces life span and carries a serious risk of co-morbidities such as those listed above.

Other diseases or disorders associated with obesity are birth defects, maternal obesity being associated with increased incidence of neural tube defects, carpal tunnel syndrome (CTS); chronic venous insufficiency (CVI); daytime sleepiness; deep vein thrombosis (DVT); end stage renal disease (ESRD); gout; heat disorders; impaired immune response; impaired respiratory function; infertility; liver disease; lower back pain; obstetric and gynecologic complications; pancreatititis; as well as abdominal hernias; acanthosis nigricans; endocrine abnormalities; chronic hypoxia and hypercapnia; dermatological effects; elephantitis; gastroesophageal reflux; heel spurs; lower extremity edema; mammegaly which causes considerable problems such as bra strap pain, skin damage, cervical pain, chronic odors and infections in the skin folds under the breasts, etc.; large anterior abdominal wall masses, for example abdominal panniculitis with frequent panniculitis, impeding walking, causing frequent infections, odors, clothing difficulties, low back pain; musculoskeletal disease; pseudo tumor cerebri (or benign intracranial hypertension), and sliding hiatil hernia.

The present invention further provides a method for increasing energy expenditure in a subject. The method includes, for example, peripherally administering a therapeutically effective amount of a compound of the invention to the subject, thereby altering energy expenditure. Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat.

In one aspect, the method of the invention involves manipulation of the arcuate circuitry, that alter food intake coordinately and reciprocally alter energy expenditure. Energy expenditure is a result of cellular metabolism, protein synthesis, metabolic rate, and calorie utilization. Thus, in this aspect of the invention, administration of a compound of formula (I) results in increased energy expenditure, and decreased efficiency of calorie utilization.

The invention also provides a method for improving a lipid profile in a subject. The invention also provides a method for alleviating a condition or disorder that can be alleviated by reducing nutrient availability.

Appetite can be measured by any means known to one of skill in the art. For example, decreased appetite can be assessed by a psychological assessment. For example, administration of a compound of the invention results in a change in perceived hunger, satiety, and/or fullness. Hunger can be assessed by any means known to one of skill in the art. For example, hunger is assessed using psychological assays, such as by an assessment of hunger feelings and sensory perception using a questionnaire, such as, but not limited to, a Visual Analog Score (VAS) questionnaire. In one specific, non-limiting example, hunger is assessed by answering questions relating to desire for food, drink, prospective food consumption, nausea, and perceptions relating to smell or taste.

A compound of the invention may be used for weight control and treatment, for example reduction or prevention of obesity, in particular any one or more of the following: preventing and reducing weight gain; inducing and promoting weight loss; and reducing obesity as measured by the Body Mass Index. A compound of the invention may be used in the control of any one or more of appetite, satiety and hunger, in particular any one or more of the following: reducing, suppressing and inhibiting appetite; inducing, increasing, enhancing and promoting satiety and sensations of satiety; and reducing, inhibiting and suppressing hunger and sensations of hunger. A compound of the invention may be used in maintaining any one or more of a desired body weight, a desired Body Mass Index, a desired appearance and good health.

A subject may be a subject who desires weight loss, for example female and male subjects who desire a change in their appearance. A subject may desire decreased feelings of hunger, for example the subject may be a person involved in a lengthy task that requires a high level of concentration, for example soldiers on active duty, air traffic controllers, or truck drivers on long distance routes, etc.

The present invention may also be used in treating, prevention, ameliorating or alleviating conditions or disorders caused by, complicated by, or aggravated by a relatively high nutrient availability. The term "condition or disorder which can be alleviated by reducing caloric (or nutrient) availability" is used herein to denote any condition or disorder in a subject that is either caused by, complicated by, or aggravated by a relatively high nutrient availability, or that can be alleviated by reducing nutrient availability, for example by decreasing food intake. Subjects who are insulin resistant, glucose intolerant, or have any form of diabetes mellitus, for example, type 1, 2 or gestational diabetes, can also benefit from methods in accordance with the present invention.

Conditions or disorders associated with increased caloric intake include, but are not limited to, insulin resistance, glucose intolerance, obesity, diabetes, including type 2 diabetes, eating disorders, insulin-resistance syndromes, and Alzheimer's disease.

According to the present invention, a compound of formula (I) is preferably used in the treatment of a human. However, while the compounds of the invention will typically be used to treat human subjects they may also be used to treat similar or identical conditions in other vertebrates for example other primates; farm animals for example swine, cattle and poultry; sport animals for example horses; companion animals for example dogs and cats.

Compositions

While it is possible for the active ingredient to be administered alone, it is preferable for it to be present in a pharmaceutical formulation or composition. Accordingly, the invention provides a pharmaceutical formulation comprising a compound of formula (I), or a variant or derivative thereof, or a salt or solvate thereof, as defined above and a pharmaceutically acceptable excipient. Pharmaceutical compositions of the invention may take the form of a pharmaceutical formulation as described below.

The pharmaceutical formulations according to the invention include those suitable for oral, parenteral (including subcutaneous, intradermal, intramuscular, intravenous, and intraarticular), inhalation (including fine particle dusts or mists which may be generated by means of various types of metered does pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2S, 1988.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition preferably does not include oxidizing agents and other compounds that are known to be deleterious to PYY and PYY agonists. Excipients that can be included are, for instance, other proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention are also suitably administered as sustained-release systems. Suitable examples of sustained-release systems of the invention include suitable polymeric materials, for example semi-permeable polymer matrices in the form of shaped articles, e.g., films, or mirocapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracistemally; intravaginally; intraperitoneally; topically, for example as a powder, ointment, gel, drop or transdermal patch; bucally; or as an oral or nasal spray.

Preparations for administration can be suitably formulated to give controlled release of compounds of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the compound of formula (I). These compositions exhibit certain biocompatibility features which allow a controlled release of the active substance. See U.S. Pat. No. 5,700,486.

A compound of the invention may be delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by a continuous subcutaneous infusions, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner. Other controlled release systems are discussed in the review by Langer (*Science* 249:1527-1533, 1990). In another aspect of the disclosure, compounds of the invention are delivered by way of an implanted pump, described, for example, in U.S. Pat. Nos. 6,436,091; 5,939,380; 5,993,414.

Implantable drug infusion devices are used to provide patients with a constant and long term dosage or infusion of a drug or any other therapeutic agent. Essentially such device may be categorized as either active or passive. A compound of the present invention may be formulated as a depot preparation. Such a long acting depot formulation can be administered by implantation, for example subcutaneously or intramuscularly; or by intramuscular injection. Thus, for example, the compounds can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of a compound of the invention may be administered as a single pulse dose, as a bolus dose, or as pulse doses administered over time. Thus, in pulse doses, a bolus administration of a compound of the invention is provided, followed by a time period wherein no a compound of the invention is administered to the subject, followed by a second bolus administration. In specific, non-limiting examples, pulse doses of a compound of the invention are administered during the course of a day, during the course of a week, or during the course of a month.

In one embodiment, a therapeutically effective amount of a compound of the invention is administered with a therapeutically effective amount of another agent, for example an additional appetite suppressant, a food-intake-reducing, plasma glucose-lowering or plasma lipid-altering agent. Specific, non-limiting examples of an additional appetite suppressant include amfepramone (diethylpropion), phentermine, mazindol and phenylpropanolamine, fenfluramine, dexfenfluramine, and fluoxetine. The compound of the invention can be administered simultaneously with the additional appetite suppressant, or it may be administered sequentially. Thus, in one embodiment, the compound of the invention is formulated and administered with an appetite suppressant as a single dose.

A compound of the invention may be administered whenever the effect, e.g., appetite suppression, decreased food intake, or decreased caloric intake, is desired, or slightly before to whenever the effect is desired, such as, but not limited to about 10 minutes, about 15 minutes, about 30 minutes, about 60 minutes, about 90 minutes, or about 120 minutes, before the time the effect is desired.

The therapeutically effective amount of a compound of the invention will be dependent on the molecule utilized, the subject being treated, the severity and type of the affliction, and the manner and route of administration. For example, a therapeutically effective amount of a compound of the invention may vary from about 0.01 µg per kilogram (kg) body weight to about 1 g per kg body weight, for example about 0.1 µg to about 20 mg per kg body weight, for example about 1 µg to about 5 mg per kg body weight, or about 5 µg to about 1 mg per kg body weight.

In one embodiment of the invention, a compound of the invention may be administered to a subject at from 5 to 1000 nmol per kg bodyweight, for example at from 10 to 750 nmol per kg bodyweight, for example at from 20 to 500 nmol per kg bodyweight, in particular at from 30 to 240 nmol per kg bodyweight. For a 75 kg subject, such doses correspond to dosages of from 375 nmol to 75 µmol, for example from 750 nmol to 56.25 µmol, for example from 1.5 to 37.5 µmol, in particular from 2.25 to 18 µmol.

In an alternative embodiment, a compound of the invention may be administered to a subject at 0.5 to 135 picomole (pmol) per kg body weight, for example 5 to 100 picomole (pmol) per kg body weight, for example 10 to 90 picomole (pmol) per kg body weight, for example about 72 pmol per kg body weight. In one specific, non-limiting example, a compound of the invention is administered in a dose of about 1 nmol or more, 2 nmol or more, or 5 nmol or more. In this example, the dose of the compound of the invention is generally not more than 100 nmol, for example, the dose is 90 nmols or less, 80 nmols or less, 70 nmols or less, 60 nmols or less, 50 nmols or less, 40 nmols or less, 30 nmols or less, 20 nmols or less, 10 nmols. For example, a dosage range may comprise any combination of any of the specified lower dose limits with any of the specified upper dose limits. Thus, examples of non-limiting dose ranges of compounds of the invention are within the range of from 1 to 100 nmols, from 2 to 90 mols, from 5 to 80 nmols.

In one specific, non-limiting example, from about 1 to about 50 nmol of a compound of the invention is administered, for example about 2 to about 20 nmol, for example about 10 nmol is administered as a subcutaneous injection. The exact dose is readily determined by one of skill in the art based on the potency of the specific compound utilized, the route of delivery of the compound and the age, weight, sex and physiological condition of the subject.

Suitable doses of compounds of the invention also include those that result in a reduction in calorie intake, food intake, or appetite, or increase in energy expenditure that is equivalent to the reduction in calorie intake, food intake, or appetite, or to increase the energy expenditure, caused by the normal postprandial level of PYY3-36. Examples of doses include, but are not limited to doses that produce the effect demonstrated when the serum levels of PYY are from about 40 pM to about 60 pM, or from about 40 pM to about 45 pM, or about 43 pM.

The disclosure is illustrated by the following non-limiting Examples.

8. EXAMPLES

Materials and Methods:

Male C57BL/6 mice (20-30 g) were used for all mouse experiments. Mice were individually housed in IVC cages. Animals were randomised by weight and fasted overnight for 16 hrs before intraperitoneal injection at 9 am. Food intake was measured at 1, 2, 3, 4, 6, 8 and 24 hours post injection. All peptide solutions were prepared freshly the morning of the study and injected as 100 ul. All statistics are calculated using a one-way ANOVA with Dunnett's post-test or one-way ANOVA with Bonferroni post-test.

Peptide Synthesis

Peptide synthesis of $PYY_{3-36}Lys_{12}$ and $PYY_{3-36}Lys_{12}$ lauryl was carried out on a tryclic amide linker resin. The sequences (except for position 12) were the human PYY sequences. Amino acids were attached using the Fmoc strategy. Each amino acid was added sequentially from the C- to the N-termini. Peptide couplings were mediated by the reagent TBTU. Peptide cleavage from the resin was achieved with trifluoracetic acid in the presence of scavengers. Native PYY(3-36) is obtained as described previously (WO03/026591); de novo synthesis using tryclic amide resin and Fmoc chemistry is also possible.

Peptides were purified by reverse phase HPLC. Full quality control was performed on all purified peptides and peptides were shown to be greater than 95% pure by HPLC in two buffer systems. Amino acid analysis following acid hydrolysis confirmed the amino acid composition. MALDI-MS showed the expected molecular ion.

Results:

Example 1

Administration of 3 Different PYY Analogues to Mice

The effects of $PYY_{3-36}$ (at 30 nmol/kg) (SEQ ID NO:2), $PYY_{3-36}Lys_{12}$ (at two dosages—60 nmol/kg and 120 nmol/kg) (SEQ ID NO:13), and $PYY_{3-36}Lys_{12}Lauryl$ (at 120 nmol/kg) (SEQ ID NO: 14), were compared after a single injection. A control of saline was used.

The results are shown in the graph of FIG. 1, in the time-interval bar charts of FIGS. 2 a) to 2 g) and in the comparative graph of FIG. 3. In the figures, $PYY_{3-36}Lys_{12}Lauryl$ is named $PYY_{3-36}Lys_{12}Acyl$. As is seen in the Figures, $PYY_{3-36}Lys_{12}Lauryl$ had a similar decreasing effect on food intake as $PYY_{3-36}$ until 8 hours. As is seen particularly in the FIG. 1 graph showing cumulative food intake, the effect of $PYY_{3-36}$ was lost after 8 hours and by 24 hours, the cumulative food intake for the 24 hour period of mice given $PYY_{3-36}$ was essentially the same as those given the saline control. That is to say that the initial decrease in food intake was compensated for by an increase in food intake between 8 and 24 hours. On the other hand, the cumulative food intake for the mice given $PYY_{3-36}Lys_{12}Lauryl$ remained below the saline control, with an overall reduction in food intake of 6.1%. The PYY$_{3-36}$Lys$_{12}$ compound had essentially the same effect as the saline.

PYY$_{3-36}$Lys$_{12}$Lauryl (at 120 nmol/kg) is seen to have the most sustained effect when compared with saline control, PYY$_{3-36}$ (at 30 nmol/kg) and PYY$_{3-36}$Lys$_{12}$ (at two dosages—60 nmol/kg and 120 nmol/kg).

Example 2

Dose Response Experiment for PYY$_{3-36}$Lys$_{12}$Lauryl in Mice

The effects of PYY$_{3-36}$Lys$_{12}$Lauryl (at three dosages—60 nmol/kg, 120 nmol/kg and 240 nmol/kg) were compared with PYY$_{3-36}$ (at 30 nmol/kg) after a single injection. A control of saline was used.

The results are shown in the time-interval bar charts of FIGS. 4 *a*) to 4 *g*) and in the comparative graph of FIG. 5. The results at the 1 hour, 2 hour and 3 hour time point (ie the amounts of food consumed in the first hour, the second hour and the third hour) show a does-response relationship, with 240 nmol/kg PYY$_{3-36}$Lys$_{12}$Lauryl achieving a greater effect than 120 nmol/kg, and both showing a greater effect than 60 nmol/kg. At all doses, the effects of PYY$_{3-36}$ and PYY$_{3-36}$Lys$_{12}$Lauryl wears off after a time and, as seen in FIG. 5, eventually the food intake becomes greater (in a given time period) in the mice that had received the PYY$_{3-36}$ and PYY$_{3-36}$ Lys$_{12}$Lauryl than in the saline control mice. The time at which that occurs is later for the PYY$_{3-36}$Lys$_{12}$Lauryl-treated mice (around 6 hours) than for the PYY$_{3-36}$-treated mice (around 4 hours) as seen in FIG. 5.

The invention claimed is:

1. A compound of formula (I):

PYY$_{3-36}$Lys$_{12}$-Acyl    (I)

wherein Acyl is an acyl group selected from the group consisting of CO—C$_{1-20}$alkyl, CO—C$_{2-20}$alkenyl, CO—C$_{5-10}$ aryl, and CO—C$_{5-10}$aryl-C$_{1-20}$alkyl; or a derivative thereof;

wherein the derivative is the compound of formula (I) that is modified by one or more processes selected from the group consisting of amidation, glycosylation, carbamylation, sulfation, phosphorylation, cyclization, lipidization, and pegylation; or a salt or solvate thereof.

2. A pharmaceutical composition comprising a compound as claimed in claim 1 and a pharmaceutically acceptable carrier.

3. A method of treating obesity or diabetes in a subject in need thereof comprising administering to the subject a compound of claim 1.

4. A method of reducing appetite in a subject, comprising administering to the subject a compound of claim 1.

5. The method of claim 3, wherein the subject is obese.

6. The method of claim 3, wherein the subject is diabetic.

7. The method of claim 3, wherein the compound is administered peripherally.

8. The method of claim 3, wherein the compound is administered subcutaneously, intravenously, intramuscularly, intranasally, transdermally or sublingually.

9. A method of treating obesity comprising administering to a subject in need thereof a compound of claim 1.

10. The method of claim 9, whereby food intake or caloric intake is reduced.

11. The method of claim 9, wherein the compound is administered peripherally.

12. The method of claim 9, wherein the compound is administered subcutaneously, intravenously, intramuscularly, intranasally, transdermally or sublingually.

13. The method of claim 4, wherein the compound is administered peripherally.

14. The method of claim 4, wherein the compound is administered subcutaneously, intravenously, intramuscularly, intranasally, transdermally or sublingually.

15. The method of claim 5, wherein the compound is administered peripherally.

16. The method of claim 5, wherein the compound is administered subcutaneously, intravenously, intramuscularly, intranasally, transdermally or sublingually.

17. The method of claim 6, wherein the compound is administered peripherally.

18. The method of claim 6, wherein the compound is administered subcutaneously, intravenously, intramuscularly, intranasally, transdermally or sublingually.

19. A method of treating a subject who is overweight comprising administering to the subject a compound of claim 1 for a time and under conditions effective to reduce the appetite of the subject.

20. The method of claim 19, wherein the compound is administered peripherally.

21. The method of claim 19, wherein the compound is administered subcutaneously, intravenously, intramuscularly, intranasally, transdermally or sublingually.

* * * * *

SEQUENCE LISTING

```
<160> NUMBER OF SEQ ID NOS: 14

<210> SEQ ID NO 1
<211> LENGTH: 36
<212> TYPE: PRT
<213> ORGANISM: Homo sapiens

<400> SEQUENCE: 1

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 2
<211> LENGTH: 34
<212> TYPE: PRT
<213> ORGANISM: Homo sapiens

<400> SEQUENCE: 2

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 3
<211> LENGTH: 36
<212> TYPE: PRT
<213> ORGANISM: Rattus sp.

<400> SEQUENCE: 3

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
        35

<210> SEQ ID NO 4
<211> LENGTH: 36
<212> TYPE: PRT
<213> ORGANISM: Sus scrofa
```

<400> SEQUENCE: 4

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
            35

<210> SEQ ID NO 5
<211> LENGTH: 36
<212> TYPE: PRT
<213> ORGANISM: Cavia porcellus

<400> SEQUENCE: 5

Tyr Pro Ser Lys Pro Glu Ala Pro Gly Ser Asp Ala Ser Pro Glu Glu
1               5                   10                  15

Leu Ala Arg Tyr Tyr Ala Ser Leu Arg His Tyr Leu Asn Leu Val Thr
            20                  25                  30

Arg Gln Arg Tyr
            35

<210> SEQ ID NO 6
<211> LENGTH: 36
<212> TYPE: PRT
<213> ORGANISM: Rana sp.

<400> SEQUENCE: 6

Tyr Pro Pro Lys Pro Glu Asn Pro Gly Glu Asp Ala Ser Pro Glu Glu
1               5                   10                  15

Met Thr Lys Tyr Leu Thr Ala Leu Arg His Tyr Ile Asn Leu Val Thr
            20                  25                  30

Arg Gln Arg Tyr
            35

<210> SEQ ID NO 7
<211> LENGTH: 36
<212> TYPE: PRT
<213> ORGANISM: Raja sp.

<400> SEQUENCE: 7

Tyr Pro Pro Lys Pro Glu Asn Pro Gly Asp Asp Ala Ala Pro Glu Glu
1               5                   10                  15

Leu Ala Lys Tyr Tyr Ser Ala Leu Arg His Tyr Ile Asn Leu Ile Thr
            20                  25                  30

Arg Gln Arg Tyr
            35

<210> SEQ ID NO 8
<211> LENGTH: 36
<212> TYPE: PRT
<213> ORGANISM: Squalus sp.

<400> SEQUENCE: 8

Tyr Pro Pro Lys Pro Glu Asn Pro Gly Glu Asp Ala Pro Pro Glu Glu
1               5                   10                  15

Leu Ala Lys Tyr Tyr Ser Ala Leu Arg His Tyr Ile Asn Leu Ile Thr
            20                  25                  30

Arg Gln Arg Tyr
            35

```
<210> SEQ ID NO 9
<211> LENGTH: 36
<212> TYPE: PRT
<213> ORGANISM: Lampetra sp.

<400> SEQUENCE: 9

Phe Pro Pro Lys Pro Asp Asn Pro Gly Asp Asn Ala Ser Pro Glu Gln
1               5                   10                  15

Met Ala Arg Tyr Lys Ala Ala Val Arg His Tyr Ile Asn Leu Ile Thr
            20                  25                  30

Arg Gln Arg Tyr
        35

<210> SEQ ID NO 10
<211> LENGTH: 36
<212> TYPE: PRT
<213> ORGANISM: Petromyzon marinus

<400> SEQUENCE: 10

Met Pro Pro Lys Pro Asp Asn Pro Ser Pro Asp Ala Ser Pro Glu Glu
1               5                   10                  15

Leu Ser Lys Tyr Met Leu Ala Val Arg Asn Tyr Ile Asn Leu Ile Thr
            20                  25                  30

Arg Gln Arg Tyr
        35

<210> SEQ ID NO 11
<211> LENGTH: 9
<212> TYPE: PRT
<213> ORGANISM: Homo sapiens

<400> SEQUENCE: 11

Ile Lys Pro Glu Ala Pro Gly Glu Asp
1               5

<210> SEQ ID NO 12
<211> LENGTH: 24
<212> TYPE: PRT
<213> ORGANISM: Homo sapiens

<400> SEQUENCE: 12

Ser Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 13
<211> LENGTH: 34
<212> TYPE: PRT
<213> ORGANISM: Artificial Sequence
<220> FEATURE:
<223> OTHER INFORMATION: Human PYY 3-36 with Ala to Lys substitution at
      position 10 (position 12 of full length PYY)

<400> SEQUENCE: 13

Ile Lys Pro Glu Ala Pro Gly Glu Asp Lys Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 14
<211> LENGTH: 34
```

```
<212> TYPE: PRT
<213> ORGANISM: Artificial Sequence
<220> FEATURE:
<223> OTHER INFORMATION: Human PYY 3-36 with acylated Lys substituted
      for Ala at position 10 (position 12 of full length PYY)
<220> FEATURE:
<221> NAME/KEY: MOD_RES
<222> LOCATION: (10)..(10)
<223> OTHER INFORMATION: Modified with acyl group

<400> SEQUENCE: 14

Ile Lys Pro Glu Ala Pro Gly Glu Asp Lys Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr
```